US010813862B2

(12) United States Patent
Klug et al.

(10) Patent No.: US 10,813,862 B2
(45) Date of Patent: Oct. 27, 2020

(54) USE OF N-METHYL-N-ACYLGLUCAMINES AS SOLUBILIZERS

(71) Applicant: Clariant International Ltd., Muttenz (CH)

(72) Inventors: Peter Klug, Grossostheim (DE); Carina Mildner, Frankfurt am Main (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/402,954

(22) PCT Filed: May 29, 2013

(86) PCT No.: PCT/EP2013/061047
§ 371 (c)(1),
(2) Date: Nov. 21, 2014

(87) PCT Pub. No.: WO2013/178671
PCT Pub. Date: Dec. 5, 2013

(65) Prior Publication Data
US 2015/0140048 A1 May 21, 2015

(30) Foreign Application Priority Data
May 30, 2012 (DE) .................. 10 2012 010 654

(51) Int. Cl.
A61K 9/70 (2006.01)
A61K 8/44 (2006.01)
A61Q 19/10 (2006.01)
A61K 8/02 (2006.01)
A61Q 19/00 (2006.01)

(52) U.S. Cl.
CPC ............. *A61K 8/44* (2013.01); *A61K 8/0208* (2013.01); *A61K 9/70* (2013.01); *A61Q 19/007* (2013.01); *A61Q 19/10* (2013.01); *A61K 2800/49* (2013.01)

(58) Field of Classification Search
None
See application file for complete search history.

(56) References Cited

U.S. PATENT DOCUMENTS

| 2,016,962 A | 10/1935 | Flint |
| 2,667,478 A | 1/1954 | Schwartz |
| 2,703,798 A | 3/1955 | Schwartz |
| 2,891,052 A | 6/1959 | Boettner |
| 2,982,737 A | 5/1961 | Boettner |
| 2,993,887 A | 7/1961 | Zech |
| 4,079,078 A | 3/1978 | Collins |
| 4,413,087 A | 11/1983 | Bernot |
| 4,505,827 A | 3/1985 | Rose |
| 4,565,647 A | 1/1986 | Llenado |
| 4,654,207 A | 3/1987 | Preston |
| 4,681,946 A | 7/1987 | Baur |
| 4,981,684 A | 1/1991 | MacKenzie |
| 5,009,814 A | 4/1991 | Kelkenberg |
| 5,194,639 A | 3/1993 | Connor |
| 5,254,281 A | 10/1993 | Pichardo |
| 5,298,195 A | 3/1994 | Brumbaugh |
| 5,317,047 A | 5/1994 | Sabate |
| 5,354,425 A | 10/1994 | MacKey |
| 5,449,770 A | 9/1995 | Shumate |
| 5,454,982 A | 10/1995 | Murch |
| 5,500,155 A | 3/1996 | Weuthen |
| 5,539,134 A | 7/1996 | Strecker |
| 5,559,078 A | 9/1996 | Garst |
| 5,560,873 A | 10/1996 | Chen |
| 5,625,098 A | 4/1997 | Kao |
| 5,691,299 A | 11/1997 | Fabry |
| 5,711,899 A | 1/1998 | Kawa |
| 5,712,235 A | 1/1998 | Nieendick |
| 5,716,922 A | 2/1998 | Curry |
| 5,750,748 A | 5/1998 | Boutique |
| 5,766,267 A | 6/1998 | Schumacher |
| 5,777,165 A | 7/1998 | Kao |
| 5,789,372 A | 8/1998 | Fabry |
| 5,874,096 A | 2/1999 | Hazen |
| 5,945,389 A | 8/1999 | Richard |

(Continued)

FOREIGN PATENT DOCUMENTS

| CA | 2127644 | 1/1995 |
| CN | 1061960 | 6/1992 |

(Continued)

OTHER PUBLICATIONS

Smith, J.T. et al., "Micellar Electrokinetic Capillary Chromatography with in Situ Charged Micelles. 1. Evaluation of N-D-Gluco-N-methylalkanamide Surfactants as Anionic Borate Complexes," Anal. Chem. 1994, 66, 1119-1133.

Söderlind, E. et al., "The usefulness of sugar surfactants as solubilizing agents in parenteral formulations," Elsevier, I nternational IJournal of Pharmaceutics 252 (2003) pp. 61-71, Aug. 19, 2002.

Tegeler, T. et al., Special Guest Editor Section: Electrically Driven Microseparation Methods for Pesticides and Metabolites: I. Micellar Electrokinetic Capillary Chromatography of Carbamate Insecticides with MEGA-Borate and SDS Surfactants, Journal of AOAC International, vol. 82, No. 6, pp. 1542-1549, Nov. 6, 1999.

(Continued)

Primary Examiner — Susan T Tran
(74) Attorney, Agent, or Firm — Tod A. Waldrop

(57) ABSTRACT

The invention relates to the use of N-methyl-N—$C_8$-$C_{14}$-acylglucamines as solubilizers in cosmetic preparations. The invention further relates to clear lotions for the preparation of wet wipes, comprising a) 0.1 to 5.0 wt.-% of the N-methyl-N—$C_8$-$C_{14}$-acylglucamines, b) 0.05 to 5% of one or more water-insoluble or only partially water-soluble anti-microbial agents, c) 0 to 5 wt.-% of one or more oils, d) 85 to 99.85 wt.-% of water, e) 0 to 5 wt.-% of surfactants, and f) 0 to 5 wt.-% of additional auxiliaries and additives.

15 Claims, No Drawings

(56) References Cited

U.S. PATENT DOCUMENTS

| | | | |
|---|---|---|---|
| 6,147,045 A | 11/2000 | Lappas | |
| 6,147,124 A | 11/2000 | Ansmann | |
| 6,165,955 A | 12/2000 | Chen | |
| 6,264,961 B1 | 7/2001 | Ansmann | |
| 6,274,126 B1 | 8/2001 | Newell | |
| 6,288,023 B1 | 9/2001 | Honda | |
| 6,329,331 B1 | 12/2001 | Aronson | |
| 6,350,788 B1 | 2/2002 | Herold | |
| 6,391,962 B2 | 5/2002 | Zerrer | |
| 6,455,001 B1 | 9/2002 | Knappe | |
| 6,727,217 B1 | 4/2004 | Nieendick | |
| 6,887,838 B2 | 5/2005 | Dykstra | |
| 6,903,057 B1 | 6/2005 | Tsaur | |
| 7,056,379 B2 | 6/2006 | Nieendick | |
| 7,217,752 B2 | 5/2007 | Schmucker-Castner | |
| 7,250,392 B1 | 7/2007 | Leonard | |
| 7,297,666 B2 | 11/2007 | Kuepper Stefan | |
| 7,407,667 B2 | 8/2008 | Zerrer | |
| 7,578,995 B2 | 8/2009 | Frantz | |
| 7,776,318 B2 * | 8/2010 | Bissey-Beugras | A61K 8/20 424/70.16 |
| 7,820,771 B2 | 10/2010 | Lapra | |
| 8,178,481 B2 | 5/2012 | Sans | |
| 8,263,538 B2 | 9/2012 | Tsaur | |
| 8,729,323 B2 | 5/2014 | Kothandaraman | |
| 8,759,255 B2 | 6/2014 | Wacker | |
| 9,187,407 B2 | 11/2015 | Koshti | |
| 9,504,636 B2 | 11/2016 | Klug | |
| 9,949,909 B2 | 4/2018 | Klug | |
| 10,172,774 B2 | 1/2019 | Klug | |
| 10,265,253 B2 | 4/2019 | Klug | |
| 2001/0023298 A1 | 9/2001 | Weinelt | |
| 2002/0004476 A1 | 1/2002 | Pancheri | |
| 2002/0065198 A1 | 5/2002 | Highsmith | |
| 2002/0168417 A1 | 11/2002 | Blease | |
| 2003/0004929 A1 | 1/2003 | Julian | |
| 2003/0049292 A1 * | 3/2003 | Turowski-Wanke | A61K 8/27 424/401 |
| 2003/0069153 A1 | 4/2003 | Jordan | |
| 2003/0199403 A1 | 10/2003 | Wells | |
| 2004/0086470 A1 | 5/2004 | Nieendick | |
| 2005/0037926 A1 | 2/2005 | Zerrer | |
| 2005/0037942 A1 | 2/2005 | Otterson | |
| 2005/0172859 A1 | 8/2005 | Nieendick | |
| 2006/0058205 A1 | 3/2006 | Ainger | |
| 2006/0079414 A1 | 4/2006 | Nieendick | |
| 2006/0100127 A1 | 5/2006 | Meier | |
| 2006/0110415 A1 | 5/2006 | Gupta | |
| 2006/0110432 A1 * | 5/2006 | Luu | A61K 8/068 424/443 |
| 2006/0135382 A1 | 6/2006 | Molenda | |
| 2006/0142291 A1 | 6/2006 | Beilfuss | |
| 2006/0166826 A1 | 7/2006 | Zerrer | |
| 2006/0171979 A1 | 8/2006 | Calvo | |
| 2007/0060489 A1 | 3/2007 | Sun | |
| 2007/0128144 A1 | 6/2007 | Bonastre | |
| 2007/0190004 A1 | 8/2007 | Bockmuhl | |
| 2007/0213226 A1 | 9/2007 | Sieverding | |
| 2009/0023622 A1 | 1/2009 | Leidreiter | |
| 2009/0253612 A1 | 10/2009 | Mushock | |
| 2009/0257972 A1 | 10/2009 | Dieker | |
| 2010/0051200 A1 | 3/2010 | Mueller | |
| 2010/0285077 A1 | 11/2010 | Lintner | |
| 2011/0002865 A1 | 1/2011 | Fournial | |
| 2011/0150786 A1 | 6/2011 | Desenne | |
| 2011/0177945 A1 | 7/2011 | Klingelhoefer | |
| 2011/0251116 A1 | 10/2011 | Aehle | |
| 2012/0009127 A1 | 1/2012 | Dasgupta | |
| 2012/0010113 A1 | 1/2012 | Hee | |
| 2012/0094890 A1 | 4/2012 | Anantaneni | |
| 2012/0172223 A1 | 7/2012 | Wacker | |
| 2012/0244092 A1 | 9/2012 | Moser | |
| 2013/0030197 A1 | 1/2013 | Harichian | |
| 2013/0189212 A1 | 7/2013 | Jawale | |
| 2013/0216491 A1 | 8/2013 | Ogihara | |
| 2014/0255330 A1 | 9/2014 | Cron | |
| 2014/0303389 A1 | 10/2014 | Crosby | |
| 2015/0032003 A1 | 1/2015 | Cho | |
| 2015/0125415 A1 | 5/2015 | Klug | |
| 2015/0126424 A1 | 5/2015 | Klug | |
| 2015/0126616 A1 | 5/2015 | Klug | |
| 2015/0133560 A1 | 5/2015 | Klug | |
| 2015/0140048 A1 | 5/2015 | Klug | |
| 2015/0141466 A1 | 5/2015 | Klug | |
| 2015/0141508 A1 | 5/2015 | Klug | |
| 2015/0150767 A1 | 6/2015 | Klug | |
| 2015/0164755 A1 | 6/2015 | Klug | |
| 2015/0164756 A1 | 6/2015 | Klug | |
| 2015/0282478 A1 | 10/2015 | Baur | |
| 2015/0320037 A1 | 11/2015 | Wacker | |
| 2015/0335550 A1 | 11/2015 | Koshti | |
| 2016/0074310 A1 | 3/2016 | Klug | |
| 2016/0136072 A1 | 5/2016 | Klug | |
| 2016/0143828 A1 | 5/2016 | Klug | |
| 2016/0243014 A1 | 8/2016 | Dahms | |
| 2016/0272666 A1 | 9/2016 | Klug | |
| 2016/0361243 A1 | 12/2016 | Klug | |
| 2017/0000710 A1 | 1/2017 | Klug | |
| 2017/0002297 A1 | 1/2017 | Klug | |
| 2017/0044434 A1 | 2/2017 | Baur | |
| 2017/0055524 A1 | 3/2017 | Baur | |
| 2017/0071199 A1 | 3/2017 | Baur | |
| 2017/0101606 A1 | 4/2017 | Klug | |
| 2017/0218293 A1 | 8/2017 | Klug | |
| 2017/0265477 A1 | 9/2017 | Baur | |
| 2017/0292062 A1 | 10/2017 | Wylde | |
| 2017/0305838 A1 | 10/2017 | Appel | |
| 2018/0215879 A1 | 8/2018 | Kupfer | |
| 2019/0076344 A1 | 3/2019 | Klug | |

FOREIGN PATENT DOCUMENTS

| | | |
|---|---|---|
| CN | 1077489 | 10/1993 |
| CN | 1078746 | 11/1993 |
| CN | 1088258 | 6/1994 |
| CN | 1140987 | 1/1997 |
| CN | 1141653 | 1/1997 |
| CN | 1155239 | 7/1997 |
| CN | 1292641 | 4/2001 |
| CN | 1296524 | 5/2001 |
| CN | 1501772 | 6/2004 |
| CN | 1518408 | 8/2004 |
| CN | 1594518 | 3/2005 |
| CN | 100528887 C | 5/2006 |
| CN | 1997341 | 7/2007 |
| CN | 102186340 | 9/2011 |
| CN | 102595882 | 7/2012 |
| CN | 103468362 | 12/2013 |
| CN | 103468382 | 12/2013 |
| CN | 104918490 | 9/2015 |
| DE | 1956509 | 5/1971 |
| DE | 2226872 A1 | 12/1973 |
| DE | 4235783 | 4/1994 |
| DE | 4435383 | 11/1995 |
| DE | 19507531 | 9/1996 |
| DE | 19701127 | 7/1998 |
| DE | 19916090 | 10/2000 |
| DE | 10117993 | 10/2002 |
| DE | 10130357 | 1/2003 |
| DE | 102007034438 | 1/2009 |
| DE | 202013011412 | 1/2014 |
| DE | 202013011413 | 1/2014 |
| DE | 102012021647 | 5/2014 |
| EP | 0048436 | 3/1982 |
| EP | 0285768 | 10/1988 |
| EP | 0285786 | 10/1988 |
| EP | 0336151 | 10/1989 |
| EP | 0378985 | 7/1990 |
| EP | 0407874 | 1/1991 |
| EP | 0539588 | 5/1993 |
| EP | 0550637 | 7/1993 |
| EP | 0572723 | 12/1993 |
| EP | 0614881 | 9/1994 |
| EP | 0633244 | 1/1995 |

(56) References Cited

FOREIGN PATENT DOCUMENTS

| | | |
|---|---|---|
| EP | 0709449 | 5/1996 |
| EP | 0745719 | 12/1996 |
| EP | 0769548 A1 | 4/1997 |
| EP | 0774503 A1 | 5/1997 |
| EP | 0995994 | 4/2000 |
| EP | 1043017 | 10/2000 |
| EP | 1078978 | 2/2001 |
| EP | 1093722 | 4/2001 |
| EP | 1110944 | 6/2001 |
| EP | 1177223 | 2/2002 |
| EP | 1379129 | 1/2004 |
| EP | 1676831 | 7/2006 |
| EP | 1716842 | 11/2006 |
| JP | S4810053 B | 2/1973 |
| JP | S63270534 | 11/1988 |
| JP | H06501731 | 2/1994 |
| JP | H06501733 | 2/1994 |
| JP | H06240599 | 8/1994 |
| JP | H07507341 | 8/1995 |
| JP | H0812993 | 1/1996 |
| JP | H0848618 | 2/1996 |
| JP | H09502476 | 3/1997 |
| JP | H09506683 | 6/1997 |
| JP | H09510956 | 11/1997 |
| JP | H10501279 | 2/1998 |
| JP | H10508043 | 8/1998 |
| JP | H11505839 | 5/1999 |
| JP | H11246890 | 9/1999 |
| JP | H11512334 | 10/1999 |
| JP | 2000512286 | 9/2000 |
| JP | 2000297028 | 10/2000 |
| JP | 2001501635 | 2/2001 |
| JP | 2001131579 | 5/2001 |
| JP | 2001247528 | 9/2001 |
| JP | 2002542344 A | 12/2002 |
| JP | 2006183030 | 7/2006 |
| JP | 2006183039 | 7/2006 |
| JP | 2007538023 | 12/2007 |
| JP | 2008110953 | 5/2008 |
| JP | 2010018586 | 1/2010 |
| JP | 2013534232 | 9/2013 |
| JP | 2014532815 | 12/2014 |
| JP | 2015518026 | 6/2015 |
| JP | 2017526776 | 9/2017 |
| WO | 9205764 A1 | 4/1992 |
| WO | 9206073 | 4/1992 |
| WO | 9206154 | 4/1992 |
| WO | 9206158 A1 | 4/1992 |
| WO | 9206161 A1 | 4/1992 |
| WO | 9206162 A1 | 4/1992 |
| WO | 9318125 | 9/1993 |
| WO | 9319149 | 9/1993 |
| WO | 9410130 | 5/1994 |
| WO | 9412608 | 6/1994 |
| WO | 9412609 | 6/1994 |
| WO | 9419941 | 9/1994 |
| WO | 9516824 | 6/1995 |
| WO | 9517880 A1 | 7/1995 |
| WO | 9519415 | 7/1995 |
| WO | 9523840 | 9/1995 |
| WO | 9533033 | 12/1995 |
| WO | 9533035 | 12/1995 |
| WO | 9603974 A1 | 2/1996 |
| WO | 9610386 | 4/1996 |
| WO | 9614374 | 5/1996 |
| WO | 9616540 | 6/1996 |
| WO | 9628023 | 9/1996 |
| WO | 9637589 | 11/1996 |
| WO | 9637592 | 11/1996 |
| WO | 9747284 A1 | 12/1997 |
| WO | 9800496 A1 | 1/1998 |
| WO | 9841601 | 9/1998 |
| WO | 9856496 | 12/1998 |
| WO | 9951716 | 10/1999 |
| WO | 0065014 | 11/2000 |
| WO | 0137658 | 5/2001 |
| WO | 0160877 | 8/2001 |
| WO | 02089575 | 11/2002 |
| WO | 2002096882 | 12/2002 |
| WO | 03000055 | 1/2003 |
| WO | 2003106457 | 12/2003 |
| WO | 2004056358 | 7/2004 |
| WO | 2004099150 | 11/2004 |
| WO | 2004099160 | 11/2004 |
| WO | 2005035486 | 4/2005 |
| WO | 2005063094 | 7/2005 |
| WO | 2005077934 | 8/2005 |
| WO | 2005117580 | 12/2005 |
| WO | 2006043635 | 4/2006 |
| WO | 2006056433 | 6/2006 |
| WO | 2006089633 | 8/2006 |
| WO | 2006100288 | 9/2006 |
| WO | 2007040280 | 4/2007 |
| WO | 2007057407 | 5/2007 |
| WO | 2007075459 | 7/2007 |
| WO | 2007101369 | 9/2007 |
| WO | 2007115643 | 10/2007 |
| WO | 2007115644 | 10/2007 |
| WO | 2007115646 | 10/2007 |
| WO | 2007141066 A1 | 12/2007 |
| WO | 2007147500 | 12/2007 |
| WO | 2007149134 | 12/2007 |
| WO | 2005085216 | 1/2008 |
| WO | 2008009360 | 1/2008 |
| WO | 2008066153 | 6/2008 |
| WO | 2008067911 | 6/2008 |
| WO | 2008104503 | 9/2008 |
| WO | 2009002956 | 12/2008 |
| WO | 2009029561 | 3/2009 |
| WO | 2009049851 | 4/2009 |
| WO | 2010005692 | 1/2010 |
| WO | 2010006713 | 1/2010 |
| WO | 2010069502 | 6/2010 |
| WO | 2010074747 | 7/2010 |
| WO | 2010074751 | 7/2010 |
| WO | 2010138661 | 12/2010 |
| WO | WO 2011138450 A2 * 11/2011 ............. A61K 8/498 |
| WO | 2012061991 | 5/2012 |
| WO | 2012116939 | 9/2012 |
| WO | 2013178668 | 12/2013 |
| WO | 2013178670 A2 | 12/2013 |
| WO | 2013178671 | 12/2013 |
| WO | 2013178679 | 12/2013 |
| WO | 2013178697 | 12/2013 |
| WO | 2013178700 | 12/2013 |
| WO | 2013178701 | 12/2013 |
| WO | 2014067663 A1 | 5/2014 |
| WO | 2014170025 | 10/2014 |
| WO | 2015082062 | 6/2015 |
| WO | 2015124302 | 8/2015 |
| WO | 2016023693 | 2/2016 |
| WO | 2016041823 | 3/2016 |

OTHER PUBLICATIONS

Zhu, Y-P, et al., "Surface Properties of N-Alkanoyl-N-Methy Glucamines and Related Materials", J. of Surfactants and Detergents, vol. 2, No. 3, Jul. 1, 1999.

Bezard (Lipids 1971;6:630-634).

Dale et al. (J. Sci. Food. Agric. 1955;6:166-170) (Year: 1955).

English Translation of Cited Excerpts of CN103468382A, Dec. 25, 2013. 2 pages.

Friedrich Vogel: "Kosmetik aus der Sicht des Chemikers", Chemie in Unserer Zeit, No. 5, Jan. 1, 1986 (Jan. 1, 1986), pp. 156-164, XP055109030, DOI: 10.1002/ciuz.19860200504 p. 160.

Hardcopy of http://igf-bingen.de/Croda_produkte.pdf, Dec. 1, 2016. 3 pages.

International Preliminary Report on Patentability for PCT/EP2013/061044, dated Feb. 12, 2014. 7 pages.

International Preliminary Report on Patentability for PCT/EP2014/001723, dated Jun. 8, 2015. 16 pages.

International Preliminary Report on Patentability for PCT/EP2015/000443, dated Jan. 22, 2016. 6 pages.

(56) References Cited

OTHER PUBLICATIONS

International Preliminary Report on Patentability for PCT/EP2015/076072, dated May 16, 2017. 5 pages.
International Search Report for PCT/EP2013/061044, dated May 15, 2014. 2 pages.
International Search Report for PCT/EP2013/061075, dated May 15, 2014. 2 pages.
International Search Report for PCT/EP2013/061076, dated May 15, 2014. 2 pages.
International Search Report for PCT/EP2013/061100, dated Jul. 16, 2014. 4 pages.
International Search Report for PCT/EP2013/061100, dated Jul. 15, 2014. 4 pages.
International Search Report for PCT/EP2014/001723, dated Jan. 5, 2015. 3 pages.
International Search Report for PCT/EP2015/000443, dated Jun. 2, 2015. 2 pages.
International Search Report for PCT/EP2015/000871 dated Jul. 15, 2015. 3 pages.
International Search Report for PCT/EP2015/076072, dated Feb. 29, 2016. 2 pages.
Mohammadi et al. Langmuir vol. 20, pp. 9657-9662; publication year: 2004.
Palm fatty acid distillate (PFAD) [online] retrieved on May 21, 2018 from: https://www.neste.com/corporate-info/sustainability/sustainable-supply-chain/pfad-residue-palm-oil-refining-process; 1 page (Year: 2018).
Plante et al. Castor Oil [online] retrieved on Jan. 13, 2016 from: http://www.dionex.com/en-us/webdocs/110518-PO-UHPLC-Castor-Oil-31May2011-LPN2822-01.pdf; 5 pages.
PubChem, Methylmeglumine, 2006. (Year: 2006) 9 pages.
Quack, et al., Fette-Seifen-Anstrichmittel 78, 200(1976). 7 pages.
R. Mohammadi, J. Wassink, A. Amirfazli, "Effect of Surfactants on Wetting of Super-Hydrophobic Surfaces", Langmuir, American Chemical Society, (Oct. 10, 2004), vol. 20, No. 22, doi:10.1021/la049268k, ISSN 07437463, pp. 9657-9662, XP055098502.
Study on Synthesis and Properties of "Green" Surfactants—Glucamine derivates, Zhao Handong, Master Thesis, Southern Yangtze University, pp. 5-6, Jul. 25, 2007.
Tan et al. (Appl Microbiol Biotechnol. 1997;47:207-211) (Year: 1997).
The Chemistry of Coconut Oil, accessed online Jul. 12, 2018 (Year: 2018) 5 pages.
V. Bergeron, P. Cooper, C. Fischer. J. Giermanska-Kahn, D. Langevin, and A. Pouchelon, "Polydimethylsiloxane (PDMS)-based antifoams" Colloids and Surfaces A: Physicochemical and Engineering Aspects 122 (1997) 103 120. 18 pages.
Walter, A.; Suchy, S.E.; Vinson, P.K., "Solubility properties of the alkylmethylglucamide surfactants", Biochimica et Biophysica Acta (BBA)—Biomembranes, Elsevier, Amsterdam, NL, Amsterdam, NL, (Nov. 2, 1990), vol. 1029, No. 1, doi:10.1016/0005-2736(90)90437-S, ISSN 0005-2736, pp. 67-74, XP023354648.
International Search Report for PCT/EP2013/061047, dated May 22, 2014.
Lichtenthaler, F.W., "Carbohydrates as Organic Raw Materials," in Ullmann's Encyclopedia of Industrial Chemistry, Wiley-VCH Verlag, 2010. (34 pages).

* cited by examiner

USE OF N-METHYL-N-ACYLGLUCAMINES AS SOLUBILIZERS

The invention relates to the use of N-methyl-N-acylglucamines as solubilizers in cosmetics preparations and also cosmetics preparations containing them, in particular lotions for producing wet wipes.

In the production of cosmetic or dermatological preparations, the problem frequently occurs that certain ingredients do not have sufficient water solubility and the preparations, in particular in the presence of salts, become hazy or form several phases. In order to avoid this, generally solubilizers or hydrotropes are added to the preparations.

WO 96/14374 describes the use of carboxylic acid N-alkyl-N-polyhydroxy-alkylamides of the formula $R^2CO—NR^3—[Z]$, in which $R^2CO$ is an aliphatic acyl radical having 1 to 8 carbon atoms, $R^3$ is hydrogen, an alkyl or hydroxyalkyl radical having 1 to 8 carbon atoms and [Z] is a polyhydroxyalkyl radical having 3 to 12 carbon atoms and 3 to 10 OH groups, as solubilizers for laundry detergents, dishwashing agents and cleaning agents, and also for cosmetics and/or pharmaceutical preparations. Those which may be mentioned as preferred are the carboxylic acid N-alkylglucamides, wherein $R^3$ is hydrogen, a methyl or octyl group, and $R^2CO$ is derived from formic acid, acetic acid, propionic acid, butyric acid or caproic acid, with the proviso that the sum of the carbon atoms in the acyl and alkyl radicals is preferably 6 to 10. Those which are cited explicitly are acetic acid N-octylglucamine, butyric acid N-octylglucamine and also caproic acid N-methylglucamine.

WO 95/16824 relates to lotions for producing wet wipes, such as wet toilet paper, containing a softening substance, an immobilizer, and also optionally a hydrophilic surfactant. As softening substance, mention may be made of fatty acid esters of $C_{12}$-$C_{28}$ fatty acids and $C_1$-$C_8$ monohydric alcohols, for example methyl palmitate, methyl stearate, isopropyl laurate, isopropyl myristate, isopropyl palmitate and ethylhexyl palmitate, and also esters of long-chain fatty alcohols with short-chain fatty acids, for example lauryl lactate or cetyl lactate. The immobilizer is intended to prevent the migration of the softening substance into the paper web and to fix it to the surface of the paper cloth. Suitable immobilizers which may be mentioned are polyhydroxy fatty acid esters and polyhydroxy fatty acid amides. Particularly preferred polyhydroxy fatty acid amides which may be mentioned are N-methyl- or N-methoxypropyl-N-acylglucamines having a straight-chain $C_{12}$-$C_{18}$ acyl group, for example N-lauryl-N-methylglucamide, N-lauryl-N-methoxypropylglucamide, N-cocoyl-N-methylglucamide, N-cocoyl-N-methoxypropylglucamide, N-palmityl-N-methoxypropylglucamide, N-talloyl-N-methylglucamide and N-talloyl-N-methoxypropylglucamide. Optional hydrophilic surfactants which may be mentioned are alkylglycosides, alkylglycoside ethers, alkylpolyethoxylated esters and also ethoxylated sorbitan mono-, di- and/or triesters of $C_{12}$-$C_{18}$ fatty acids.

It is the object of the invention to provide solubilizers having an improved solubilization capacity for producing cosmetics preparations.

The object is achieved by the use of N-methyl-N—$C_8$-$C_{14}$-acylglucamines as solubilizers in cosmetics preparations.

It has been found that N-methyl-N-acylglucamines having a high fraction of $C_3$-$C_{14}$ acyl exhibit a particularly high solubilization capacity. N-Methyl-N-acylglucamines of these chain lengths are outstandingly suitable for producing clear solutions of water-insoluble and only partially water-soluble substances, and therefore for producing stable wet-wipe lotions.

N-Methyl-N-acylglucamines have the formula (I),

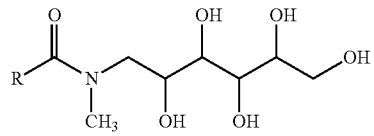

where R is an alkyl radical or a monounsaturated or polyunsaturated alkenyl radical, and in the case of $C_8$-$C_{14}$ acylglucamines, therefore, a $C_7$-$C_{13}$ alkyl or a monounsaturated or polyunsaturated alkenyl radical.

Generally, N-methyl-N-acylglucamines used according to the invention contain at least 80% by weight of N-methyl-N-acylglucamines which contain a $C_8$-$C_{14}$ acyl group. Particularly preferably, the fraction of N-methyl-N-acylglucamines which contain a $C_8$-$C_{14}$ acyl group is at least 90% by weight. In addition, the N-methyl-N-acylglucamines used according to the invention as solubilizers contain small fractions of N-methyl-N-acylglucamines derived from short-chain and/or long-chain fatty acids, in particular those which contain $C_1$-$C_4$ acyl, $C_6$ acyl, $C_{18}$ acyl and/or $C_{20}$ acyl.

In one embodiment of the invention, N-methyl-N-acylglucamines are used, wherein at least 80% by weight of the N-methyl-N-acylglucamines contain a $C_8$ acyl, or a $C_{10}$ acyl group.

In a further embodiment of the invention, N-methyl-N-acylglucamines are used, wherein at least 80% by weight of the N-methyl-N-acylglucamines contain a $C_{12}$ acyl or a $C_{14}$ acyl group.

In a further embodiment of the invention, N-methyl-N-acylglucamines are used which consist exclusively of N-methyl-N-acylglucamines which contain a $C_8$ acyl, $C_{10}$ acyl, $C_{12}$ acyl, or a $C_{14}$ acyl group or mixtures thereof.

The N-methyl-N-acylglucamines can, as described in EP 0 550 637 B1, be prepared by reacting the corresponding fatty acid esters or fatty acid ester mixtures with N-methylglucamine in the presence of a solvent having hydroxyl groups or alkoxy groups. Suitable solvents are, for example, $C_1$-$C_4$ monohydric alcohols, ethylene glycol, propylene glycol, glycerol, and also alkoxylated alcohols. Preference is given to 1,2-propylene glycol. N-methylglucamine can, as likewise described in EP 0 550 637 A1, be obtained by reductive amination of glucose with methylamine.

Suitable fatty acid esters which are reacted with the N-methylglucamines to form N-methyl-N-acylglucamines are generally the methyl esters which are obtained by transesterification from natural fats and oils, for example the triglycerides.

Suitable raw materials for the preparation of the fatty acid methyl esters are, for example, coconut oil or palm oil. The N-methyl-N-acylglucamines used according to the invention are suitable as solubilizers for producing skin and hair treatment compositions. Examples are body washes, shower creams, skincare compositions, day creams, night creams, care creams, nutrient creams, body lotions and ointments. The N-methyl-N-acylglucamines used according to the invention are suitable as solubilizers for producing oil-in-water emulsions, preferably for the treatment or care of the skin.

Skin-care compositions such as creams and lotions generally, in addition to the said oils, have surfactants, emulsifiers, fats, waxes, stabilizers, refitting agents, thickeners, biogenic active ingredients, film-forming agents, preservatives, colorants and fragrances.

In a particularly preferred embodiment, the N-methyl-N-acylglucamines are used as solubilizers in lotions for producing wet wipes.

Such lotions, in addition to the N-methyl-N-acylglucamines, contain at least one or more water-insoluble or only partially water-soluble antimicrobial active ingredients b), optionally oils c), water d), optionally surfactants e), and also optionally further customary auxiliaries and additives f) and preferably exhibit a clear appearance. It is understood here that the composition is optically transparent at a layer thickness of 5 cm and does not appear opaque and emulsion-like. In addition, the compositions do not exhibit separation into a plurality of phases and are therefore homogeneous.

Water-insoluble or only partially water-soluble antimicrobial active ingredients b) are preferably phenoxyethanol, benzyl alcohol, phenethyl alcohol, 1,2-octanediol, ethylhexyl glycerol, sorbitan caprylate, glyceryl caprylate, parabens, or contain mixtures of two or more thereof. Particular preference is given to benzyl alcohol and phenoxyethanol.

The oil content of the lotions is generally up to 5% by weight, preferably up to 2% by weight, based on all components of the lotion.

The oils c) are preferably selected from the group of natural and synthetic fats, such as the triglycerides, preferably of esters of fatty acids with alcohols of low carbon number such as isopropanol, propylene glycol or glycerol, or of esters of long-chain fatty alcohols with alkanoic acids of low carbon number or alkyl benzoates, and also natural or synthetic hydrocarbon oils.

Triglycerides of linear or branched, saturated or unsaturated, optionally hydroxylated, $C_8$-$C_{30}$ fatty acids come into consideration, in particular vegetable oils, such as sunflower, maize, soy, rice, jojoba, babusscu, pumpkin, grapeseed, sesame, walnut, apricot, orange, wheatgerm, peach kernel, macadamia, avocado, sweet almond, lady's smock, castor oil, olive oil, peanut oil, rapeseed oil and coconut oil, and also synthetic triglyceride oils, e.g. the commercial product Myritol® 318. Hardened triglycerides are also preferred according to the invention. Oils of animal origin, for example beef tallow, perhydrosqualene and lanolin can also be used.

A further class of preferred oils are the benzoic acid esters of linear or branched $C_{8-22}$ alkanols, e.g. the commercial products Finsolv® SB (isostearyl benzoate), Finsolv® TN ($C_{12}$-$C_{15}$ alkyl benzoate) and Finsolv® EB (ethylhexyl benzoate).

A further class of preferred oils are the dialkyl ethers having in total 12 to 36 carbon atoms, in particular having 12 to 24 carbon atoms, such as, e.g., di-n-octyl ether (Cetiol® OE), di-n-nonyl ether, di-n-decyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether, di-3-ethyldecyl ether, tert-butyl n-octyl ether, isopentyl n-octyl ether and 2-methylpentyl n-octyl ether, and also di-tert-butyl ether and diisopentyl ether.

Branched saturated or unsaturated fatty alcohols having 6-30 carbon atoms also come into consideration, e.g. isostearyl alcohol, and also Guerbet alcohols.

A further class of preferred oils are hydroxycarboxylic acid alkyl esters. Preferred hydroxycarboxylic acid alkyl esters are full esters of glycolic acid, lactic acid, malic acid, tartaric acid or citric acid. Further esters suitable in principle of hydroxycarboxylic acids are esters of R-hydroxypropionic acid, of tartronic acid, of D-gluconic acid, saccharic acid, mucic acid or glucuronic acid. As alcohol component of these esters, primary, linear or branched aliphatic alcohols having 8 to 22 carbon atoms are suitable. In this case, the esters of $C_{12}$-$C_{15}$ fatty alcohols are particularly preferred.

Esters of this type are commercially available, e.g. under the trade name Cosmacol® from EniChem, Augusta Industriale.

A further class of preferred oils are dicarboxylic acid esters of linear or branched $C_2$-$C_{10}$ alkanols, such as di-n-butyl adipate (Cetiol® B), di-(2-ethylhexyl) adipate and di-(2-ethylhexyl) succinate and also diol esters such as ethylene glycol dioleate, ethylene glycol diisotridecanoate, propylene glycol di-(2-ethylhexanoate), propylene glycol diisostearate, propylene glycol dipelargonate, butanediol diisostearate and neopentyl glycol dicaprylate and also diisotridecyl azelate.

Oils which are equally preferred are symmetrical, unsymmetrical or cyclic esters of carbonic acid with fatty alcohols, glycerol carbonate or dicaprylyl carbonate (Cetiol® CC).

A further class of preferred oils are the esters of dimeric unsaturated $C_{12}$-$C_{22}$ fatty acids (dimer fatty acids) with monohydric linear, branched or cyclic $C_2$-$C_{18}$ alkanols, or with polyhydric linear or branched $C_2$-$C_6$ alkanols.

A further class of preferred oils is hydrocarbon oils, for example those having linear or branched, saturated or unsaturated $C_7$-$C_{40}$ carbon chains, for example Vaseline, dodecane, isododecane, cholesterol, lanolin, synthetic hydrocarbons such as polyolefins, in particular polyisobutene, hydrogenated polyisobutene, polydecane, also hexadecane, isohexa-decane, paraffin oils, isoparaffin oils, e.g. the commercial products of the Permethyl® series, squalene, squalane, and alicyclic hydrocarbons, e.g. the commercial product 1,3-di-(2-ethylhexyl)cyclohexane (Cetiol® S).

Preferred oils are triglycerides, in particular triglycerides of caprylic acid and/or capric acid, termed dialkyl ethers, in particular dicapryl ether, and also dicapryl carbonate.

The invention also relates to lotions for producing wet wipes containing a) N-methyl-N—$C_8$-$C_{14}$-acylglucamines as described above, b) one or more water-insoluble or only partially water-soluble antimicrobial active ingredients, c) optionally one or more oils, d) water, e) optionally surfactants, f) optionally further auxiliaries and additives.

Generally, the lotions according to the invention contain a) 0.1 to 5.0% by weight, preferably 0.2 to 3.0% by weight, of the N-methyl-N-acylglucamines, b) 0.05 to 5% by weight, preferably 0.1 to 2% by weight, particularly preferably 0.2 to 1.5% by weight, of one or more water-insoluble or only partially water-soluble antimicrobial active ingredients, c) 0 to 5% by weight, preferably 0 to 2% by weight, of one or more oils, d) 85 to 99.85% by weight, preferably 90 to 98% by weight, of water, e) 0 to 5% by weight, preferably 0 to 2% by weight, of surfactants, f) 0 to 5% by weight, preferably 0 to 2% by weight, of further auxiliaries and additives, wherein the total of components a) to f) is 100% by weight.

The invention also relates to the wet wipes themselves impregnated with the lotion according to the invention.

The optional surfactants e) can be nonionic surfactants, anionic surfactants, cationic surfactants and amphoteric surfactants.

Anionic surfactants which come into consideration are ($C_{10}$-$C_{22}$) alkyl and alkylene carboxylates, alkyl ether carboxylates, fatty alcohol sulfates, fatty alcohol ether sulfates, alkylamide sulfates and alkylamide sulfonates, fatty acid alkyl amide polyglycol ether sulfates, alkanesulfonates and hydroxy-alkane sulfonates, olefin sulfonates, acyl esters of isethionates, α-sulfo fatty acid esters, alkylbenzene sulfonates, alkylphenol glycol ether sulfonates, sulfosuccinates, sulfosuccinic acid semiesters and diesters, fatty alcohol phosphates, fatty alcohol ether phosphates, protein-fatty acid condensation products, alkyl monoglyceride sulfates and alkyl monoglyceride sulfonates, alkylglyceride ether sulfonates, fatty acid methyl-taurides, fatty acid sarcosinates, sulfosuccinates, sulforicinoleates, acyl glutamates and acyl glycinates. These compounds and mixtures thereof are used in the form of their water-soluble or water-dispersible salts, for example the sodium, potassium, magnesium, ammonium, mono-, di- and triethanolammonium, and also analogous alkylammonium salts.

Suitable cationic surfactants are substituted or unsubstituted straight-chain or branched quaternary ammonium salts of the $R^1N(CH_3)_3X$, $R^1R^2N(CH_3)_2X$, $R^1R^2R^3N(CH_3)X$ or $R^1R^2R^3R^4NX$ type. The radicals $R^1$, $R^2$, $R^3$ and $R^4$ can preferably be independently of one another unsubstituted alkyl having a chain length of between 8 and 24 carbon atoms, in particular between 10 and 18 carbon atoms, hydroxyalkyl having 1 to 4 carbon atoms, phenyl, $C_2$ to $C_{18}$ alkenyl, $C_7$ to $C_{24}$ aralkyl, $(C_2H_4O)_xH$, wherein x is from 1 to 3, alkyl radicals containing one or more ester groups, or cyclic quaternary ammonium salts. X is a suitable anion. Preference is given to ($C_8$-$C_{22}$) alkyltrimethylammonium chloride or bromide, particularly preferably cetyltrimethylammonium chloride or bromide, di-($C_8$-$C_{22}$) alkyldimethylammonium chloride or bromide, ($C_8$-$C_{22}$) alkyldimethyldibenzylammonium chloride or bromide, ($C_8$-$C_{22}$) alkyldimethylhydroxy-ethylammonium chloride, phosphate, sulfate, lactate, particularly preferably distearyldimethylammonium chloride, di($C_8$-$C_{22}$) alkylaminopropyltrimethylammonium chloride and methosulfate.

Nonionic surfactants which come into consideration, for example, are the following compounds:

- polyethylene, polypropylene and polybutylene oxide condensates of alkylphenols. These compounds comprise the condensation products of alkylphenols having a $C_6$ to $C_{20}$ alkyl group which can either be linear or branched, with alkene oxides. These surfactants are termed alkylphenol alkoxylates, e.g. alkylphenol ethoxylates.
- condensation products of aliphatic alcohols with 1 to 25 mol of ethylene oxide. The alkyl or alkenyl chain of the aliphatic alcohols can be linear or branched, primary or secondary, and generally contains 8 to 22 carbon atoms. Particular preference is given to the condensation products of $C_{10}$ to $C_{20}$ alcohols having 2 to 18 mol of ethylene oxide per mole of alcohol. The alcohol ethoxylates can have a narrow homolog distribution of the ethylene oxide ("narrow range ethoxylates") or a broad homolog distribution of the ethylene oxide ("broad range ethoxylates"). Examples of commercially available nonionic surfactants of this type are Tergitol® 15-S-9 (condensation product of a linear secondary $C_{11}$-$C_{15}$ alcohol with 9 mol of ethylene oxide), Tergitol® 24-L-NMW (condensation product of a linear primary $C_{12}$-$C_{14}$ alcohol with 6 mol of ethylene oxide having a narrow molar mass distribution). Likewise, the Genapol® brands from Clariant, fall under this class of product.
- condensation products of ethylene oxide with a hydrophobic base formed by condensation of propylene oxide with propylene glycol. The hydrophobic part of these compounds preferably has a molecular weight between 1500 and 1800. The attachment of ethylene oxide to this hydrophobic part leads to an improvement in water solubility. The product is liquid up to a polyoxyethylene content of approximately 50% of the total weight of the condensation product, which corresponds to a condensation with up to approximately 40 mol of ethylene oxide. Commercially available examples of this class of product are the Pluronic® brands from BASF and the Genapol® PF brands from Clariant.
- condensation products of ethylene oxide with a reaction product of propylene oxide and ethylenediamine. The hydrophobic unit of these compounds consists of the reaction product of ethylenediamine with excess propylene oxide and generally has a molecular weight of from 2500 to 3000. To this hydrophobic unit is added ethylene oxide up to a content of 40 to 80% by weight of polyoxyethylene and a molecular weight of from 5000 to 11 000. Commercially available examples of this class of compound are the Tetronic® brands from BASF and the Genapol® PN brands from Clariant.

Further suitable nonionic surfactants are alkyl and alkenyl oligoglycosides and also fatty acid polyglycol esters or fatty amine polyglycol esters each having 8 to 20, preferably 12 to 18, carbon atoms in the fatty alkyl radical, alkyl oligoglycosides, alkenyl oligoglycosides and fatty acid N-alkyl-glucamides.

In addition, the compositions according to the invention can contain amphoteric surfactants. These can be described as derivatives of long-chain secondary or tertiary amines which have an alkyl group having 8 to 18 carbon atoms and in which a further group is substituted with an anionic group which imparts the water solubility, for instance, e.g., with a carboxyl, sulfate or sulfonate group. Preferred amphoteric surfactants are N—($C_{12}$-$C_{18}$)-alkyl-β-aminopropionates and N—($C_{12}$-$C_{18}$)-alkyl-β-imino-dipropionates as alkali metal salts and mono-, di- and trialkylammonium salts. Suitable further surfactants are also amine oxides. These are oxides of tertiary amines with a long-chain group of 8 to 18 carbon atoms and two usually short-chain alkyl groups having 1 to 4 carbon atoms. Preference here is given, for example, to the $C_{10}$ to $C_{18}$ alkyldimethylamine oxides, fatty acid amido alkyldimethylamine oxide.

Auxiliaries and additives f) are, for example, emulsifiers, preservatives and fragrances.

As emulsifiers, the following preferably come into consideration: addition products of 0 to 30 mol of ethylene oxide and/or 0 to 5 mol of propylene oxide to linear fatty alcohols having 8 to 22 carbon atoms, to fatty acids having 12 to 22 carbon atoms, to alkylphenols having 8 to 15 carbon atoms in the alkyl group and to sorbitan or sorbitol esters; ($C_{12}$-$C_{18}$) fatty acid mono- and diesters of addition products of 0 to 30 mol of ethylene oxide to glycerol; glycerol monoesters and diesters and sorbitan mono- and diesters of saturated and unsaturated fatty acids having 6 to 22 carbon atoms and optionally the ethylene oxide addition products thereof; addition products of 15 to 60 mol of ethylene oxide to castor oil and/or hardened castor oil;

polyol esters, and in particular polyglycerol esters, such as, e.g., polyglycerol polyricinoleate and polyglycerol poly-12-hydroxystearate.

Equally preferably suitable are ethoxylated fatty amines, fatty acid amides, fatty acid alkanolamides and mixtures of compounds from a plurality of these classes of substance.

As preservatives, the preservatives that are listed in the relevant annex of the European cosmetics legislation are suitable. Examples are benzoic acid and sorbic acid, and particularly highly suitable is, for example, 1,3-bis-(hydroxymethyl)-5,5-dimethylimidazolidine-2,4-dione (Nipaguard®DMDMH).

As fragrances, individual odorant compounds, e.g. the synthetic products of the type of esters, ethers, aldehydes, ketones, alcohols and hydrocarbons can be used. Odorant compounds of the ester type are, e.g., benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether, and the aldehydes include, e.g., the linear alkanols having 8 to 18 carbon atoms, citral, citronellal, citronellyloxyacetaldehyde, cyclamen aldehyde, hydroxycitronellal, lilial and bourgeonal, the ketones include, e.g., the ionones, alpha-isomethylionone and methyl cedryl ketone, the alcohols include anethole, citronellol, eugenol, geranion, linalool, phenylethyl alcohol and terpineol, and the hydrocarbons include principally the terpenes and balsams. Preferably, mixtures of various odorants are used which together generate an appropriate fragrance.

As fragrances, natural odorant mixtures can also be comprised, as are accessible from plant or animal sources, e.g. pine oil, citrus oil, jasmine oil, lily oil, rose oil, or ylang-ylang oil. Essential oils of low volatility which are usually used as aroma components, are also suitable as perfume oils, e.g. sage oil, chamomile oil, clove oil, lemon balm oil, mint oil, cinnamon leaf oil, lime blossom oil, juniper berry oil, vetiver oil, frankincense oil, galbanum oil and ladanum oil.

The invention will be explained in more detail by the examples hereinafter.

EXAMPLES

Examples 1 to 5 and Also Comparative Examples 1 and 2

The N-acyl-N-methylglucamines described hereinafter were prepared according to EP 0 550 637 from the corresponding fatty acid methyl esters and N-methylglucamine in the presence of 1,2-propylene glycol as solvent and obtained as solid comprising active substance and 1,2-propylene glycol (all figures in % by weight). Mixtures of N-acyl-N-methylglucamines with acyl radicals of the stated carbon numbers were obtained (C8/C10 and/or C12/C14).

TABLE 1

| Example | Methyl esters | Active substance (%) | 1,2-Propylene glycol (%) | Melting point |
|---|---|---|---|---|
| Example 1 | C12/14 | 90 | 10 | 85 |
| Example 2 | C8/10 | 90 | 10 | 50 |

The viscosities were measured using a Brookfield viscometer model DV II, with the spindles from spindle set RV at 20 revolutions/minute and at 20° C. Spindles 1 to 7 from the spindle set RV were used. Under these measurement conditions, spindle 1 was selected for viscosities of a maximum of 500 mPa·s, spindle 2 for viscosities of a maximum of 1000 mPa·s, spindle 3 for viscosities of a maximum of 5000 mPa·s, spindle 4 for viscosities of a maximum of 10000 mPa·s, spindle 5 for viscosities of a maximum of 20000 mPa·s, spindle 6 for viscosities of a maximum of 50000 mPa·s and spindle 7 for viscosities of a maximum of 200000 mPa·s.

Solubilizer tests were carried out. As test oil phase 1, a mixture of phenoxyethanol/benzyl alcohol/sorbitanic caprylate (Velsan® SC) in the ratio 1:1:1 was used. The usage rate was 1.5% by weight.

The test oil phase and increasing amounts of solubilizer (0.5/1/1.5/2/2.5% of active substance) were mixed and made up to 100% with water at 20 to 25° C. with stirring. The turbidity of the solution was assessed after 30 min. Turbid formulations were further heated to approximately 60° C. after evaluation, and after cooling they were evaluated again. The lowest concentration at which the solution became clear was noted (all figures in % by weight).

TABLE 2

| Solubilizer | Solubilizer | Chain fraction | Clear solution from | Observation |
|---|---|---|---|---|
| Example 3 | Example 1 | C 12/14 | 2.0% | |
| Example 4 | Example 2 | C 8/10 | 1.5% | |
| Comparative example 1 | Glucopon 215 (C8/10-alkylpolyglucoside) | | 2.0% | only after additional heating |

As may be seen in table 2, the C8/10 and C12/14-N/acyl-N-methylglucamines exhibit clear solutions at lower initial concentrations compared with comparative example 1, even without additional heating.

As test oil phase 2, a mixture of phenoxyethanol/benzyl alcohol/sorbitan caprylate (Velsan® SC)/dicaprylyl ether=1:1:1:1 was used. The usage rate was 2.0% by weight.

The test oil phase and an increasing amount of solubilizer (0.5/1/1.5/2/2.5% by weight of active substance) were mixed and made up to 100% with water at 20-25° C. with stirring. The turbidity of the solution was evaluated after 30 min. Turbid formulations were heated once more to approximately 60° C. after evaluation, and after they had cooled were evaluated again. The lowest concentration at which the solution became clear was noted (all figures in % by weight).

TABLE 3

| Solubilizer | Solubilizer | Chain fraction | Clear solution from | Observation |
|---|---|---|---|---|
| Example 5 | Example 1 | C 12/14 | 2.0% | |
| Example 6 | Example 2 | C 8/10 | 2.5% | |
| Comparative example 2 | Glucopon 215 (C8/10-alkylpolyglucoside) | | 3.0% | only after additional heating |

As may be seen in table 3, the N-acyl-N-methylglucamines according to the invention exhibit clear solutions at a low starting concentration compared with alkylpolyglucosides, even without additional heating.

The invention claimed is:

1. A composition for producing wet wipes containing
   a) 0.1 to 5.0% by weight of a mixture of N-methyl-N—$C_8$-$C_{14}$-acylglucamines wherein at least 80% by weight of the N-methyl-N-acylglucamines have a $C_8$-$C_{10}$ acyl group,
   b) 0.05 to 5% by weight of one or more water-insoluble or only partially water-soluble antimicrobial active ingredients selected from the group consisting of phenyoxyethanol, benzyl alcohol, phenethyl alcohol, 1,2-octanediol, ethylhexyl glycerol, sorbitan caprylate, glyceryl caprylate and parabens, provided that sorbitan caprylate is one of the ingredients,
   c) 0 to 5% by weight of one or more oils,
   d) 85 to 99.85% by weight of water,
   e) 0 to 5% by weight of surfactants, and
   f) 0 to 5% by weight of further auxiliaries and additives,
   wherein the composition is in the form of a clear lotion, the lotion being optically transparent at a layer thickness of 5 cm.

2. The clear lotion as claimed in claim 1, wherein it contains at least one oil selected from the group consisting of dicapryl ether, triglycerides of caprylic and/or capric acid and dicapryl carbonate.

3. A wet wipe which is impregnated with the clear lotion as claimed in claim 1.

4. A process for producing the clear solution as claimed in claim 1, comprising the step of adding to the clear solution a mixture of N-methyl-N—$C_8$-$C_{14}$-acylglucamines as a solubilizer.

5. The composition as claimed in claim 1, wherein the total of components a) to f) is 100% by weight.

6. The composition as claimed in claim 1, wherein the composition does not exhibit separation into a plurality of phases.

7. The composition as claimed in claim 1, wherein b) is a combination of sorbitan caprylate, phenoxyethanol and benzyl alcohol.

8. A composition for producing wet wipes containing
   a) 0.1 to 5.0% by weight of a mixture of N-methyl-N—$C_8$-$C_{14}$-acylglucamines wherein at least 80% by weight of the N-methyl-N-acylglucamines have a $C_8$-$C_{10}$ acyl group,
   b) 0.05 to 5% by weight of sorbitan caprylate,
   c) 0 to 5% by weight of one or more oils,
   d) 85 to 99.85% by weight of water,
   e) 0 to 5% by weight of surfactants, and
   f) 0 to 5% by weight of further auxiliaries and additives,
   wherein the composition is in the form of a clear lotion, the lotion being optically transparent at a layer thickness of 5 cm.

9. The clear lotion as claimed in claim 8, wherein it contains at least one oil selected from the group consisting of dicapryl ether, triglycerides of caprylic and/or capric acid and dicapryl carbonate.

10. A wet wipe which is impregnated with the clear lotion as claimed in claim 8.

11. The composition as claimed in claim 8, wherein the total of components a) to f) is 100% by weight.

12. The composition as claimed in claim 8, wherein the composition does not exhibit separation into a plurality of phases.

13. The composition as claimed in claim 8, wherein the sorbitan caprylate is present in an amount of 0.2 to 1.5% by weight.

14. The composition as claimed in claim 8, wherein the sorbitan caprylate is present in an amount of 0.1 to 2% by weight.

15. The composition as claimed in claim 8, wherein the total of components a) to f) is 100% by weight.

* * * * *